(12) United States Patent
Tusher et al.

(10) Patent No.: US 7,363,165 B2
(45) Date of Patent: Apr. 22, 2008

(54) SIGNIFICANCE ANALYSIS OF MICROARRAYS

(75) Inventors: Virginia Goss Tusher, Palo Alto, CA (US); Robert Tibshirani, Palo Alto, CA (US); Gilbert Chu, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 361 days.

(21) Appl. No.: 09/811,762

(22) Filed: Mar. 19, 2001

(65) Prior Publication Data

US 2002/0019704 A1 Feb. 14, 2002

Related U.S. Application Data

(60) Provisional application No. 60/208,073, filed on May 4, 2000.

(51) Int. Cl.
*G06F 19/00* (2006.01)
*C12Q 1/68* (2006.01)

(52) U.S. Cl. ............................. 702/19; 435/6; 702/20
(58) Field of Classification Search .................. 702/19, 702/20; 435/6
See application file for complete search history.

(56) References Cited

U.S. PATENT DOCUMENTS

| 5,840,484 A | | 11/1998 | Seilhamer et al. ............. 435/6 |
| 5,908,978 A | * | 6/1999 | Amerson et al. ........... 800/319 |
| 6,114,114 A | | 9/2000 | Seilhamer et al. ............. 435/6 |

FOREIGN PATENT DOCUMENTS

| EP | 0717113 A2 | 6/1996 |
| EP | 0848067 A2 | 6/1998 |
| EP | 0935210 A2 | 8/1999 |
| WO | WO 97/10365 | 3/1997 |
| WO | WO 99/58720 | 11/1999 |
| WO | WO 99/60450 | 11/1999 |
| WO | WO 00/28091 | 5/2000 |
| WO | WO 00/71756 A1 | 11/2000 |

OTHER PUBLICATIONS

International Search Report mailed Aug. 31, 2001.

"Distinct types of diffuse large B-cell lymphoma identified by gene expression profiling," A. Alizadeh et al., *Nature*, vol. 403, Feb. 3, 2000, pp. 503-511.
"Cluster analysis and display of genome-wide expression patterns," M.B. Eisen et al., *Proc. Natl. Acad. Sci. USA*, vol. 95, Dec. 1998, pp. 14863-14868.
"Ploidy Regulation of Gene Expression," T. Galitski et al., *Science*, vol. 285, Jul. 9, 1999, pp. 251-254.
"Signaling and Circuitry of Multiple MAPK Pathways Revealed by a Matrix of Global Gene Expression Profiles," C. J. Roberts et al., *Science*, vol. 287, Feb. 4, 2000, pp. 873-880.
"An Informative-Intensive Apparoach to the Molecular Pharmacology of Cancer," J.N. Weinstein et al., *Science*, vol. 275, Jan. 17, 1997, pp. 343-349.
Dialog Search dated Mar. 21, 2000.
Dialog Search dated Apr. 6, 2000.
Dialog Search dated Apr. 11, 2000.
Dialog Search dated Apr. 4, 2000.
"Molecular Classification of Cancer: Class Discovery and Class Prediction by Gene Expression Monitoring," T.R. Golub et al., *Science*, vol. 286, Oct. 15, 1999, pp. 531-537.

* cited by examiner

*Primary Examiner*—Lori A. Clow
(74) *Attorney, Agent, or Firm*—Wong, Cabello, Lutsch, Rutherford & Brucculeri, LLP (57) ABSTRACT

Microarrays can measure the expression of thousands of genes and thus identify changes in expression between different biological states. Methods are needed to determine the significance of these changes, while accounting for the enormous number of genes. We describe a new method, Significance Analysis of Microarrays (SAM), that assigns a score to each gene based on the change in gene expression relative to the standard deviation of repeated measurements. For genes with scores greater than an adjustable threshold, SAM uses permutations of the repeated measurements to estimate the percentage of such genes identified by chance, the false discovery rate (FDR). When the transcriptional response of human cells to ionizing radiation was measured by microarrays, SAM identified 34 genes that changed at least 1.5-fold with an estimated FDR of 12%, compared to FDRs of 60% and 84% using conventional methods of analysis. Of the 34 genes, 19 were involved in cell cycle regulation, and 3 in apoptosis. Surprisingly, 4 nucleotide excision repair genes were induced, suggesting that this repair pathway for UV-damaged DNA might play a heretofore unrecognized role in repairing DNA damaged by ionizing radiation.

30 Claims, 6 Drawing Sheets

SIGNIFICANCE ANALYSIS OF MICROARRAYS

CROSS REFERENCE TO RELATED APPLICATION

This application claims the benefit of U.S. Provisional Application Ser. No. 60/208,073, filed May 4, 2000, which is hereby incorporated by reference in its entirety for all purposes.

BACKGROUND OF THE INVENTION

This invention relates in general to statistical analysis of gene related data and, in particular, to analysis of microarray data for identifying genes that exhibit statistically significant behavior.

Different biological systems are characterized by differences in the copy number of genes or in levels of transcription of particular genes. By measuring such biological phenomena, insight into and possible treatment of human diseases may be found.

Microarrays of various types have been employed for measuring the expression levels of large numbers of genes. One type of microarray is the oligonucleotide microarray, one example of which is the Gene Chip® microarray manufactured by Affymetrix corporation of California. International Patent Application PCT/US96/14839, which is incorporated herein in its entirety, describes a method for measuring gene expression levels using oligonucleotide microarrays. In the method described, a nucleic acid sample is hybridized to a high density array of oligonucleotide probes immobilized to a surface, where the high density array contains oligonucleotide-type probes complementary to sequences of the target nucleic acids in the nucleic acid sample. For example, RNA transcripts of one or more target genes may be hybridized to an array of oligonucleotide probes immobilized on a surface such as that of a semiconductor chip. Some of the probes on the surface have sequences that are perfectly complementary to particular target sequences and are referred to herein as perfect match (PM) probes. Also present on the chip are probes whose sequence is deliberately selected not to be perfectly complementary to a target sequence. Such probes are referred to as mismatched (MM) control probes, where for each PM probe, there is a MM control probe for the same particular target sequence. This mismatch may comprise one or more bases. Thus, the biological sample such as a mRNA sample can be analyzed for gene expression for hybridization to above-described microarray on a chip. The presence of RNA sequences that bind to the oligonucleotide probes on the chips are then detected by methods such as tagging with a fluorescence material and then detecting the fluorescence. Since sequences that are different from the target sequences may also bind to the PM probes that correspond to such target sequences, the fluorescence signals from such sequences would appear as noise. Signal-to-noise ratio is improved by calculating the difference from signals from the sequences that bind to the PM probes and the signals from sequences that bind to the MM probes.

Another type of microarray that has been used for analyzing gene expression utilizes cDNA probes. Although massive amounts of data are generated using oligonucleotide or cDNA probes, quantitative methods are needed to determine whether differences in gene expression are experimentally significant. Previous work on microarrays has utilized cluster analysis, to find coherent in expression patterns among genes or in cells. See, for example, the following three articles:

1. Alizadeh, A., Eisen, M., Davis, R., Ma, C., Lossos, I., Rosenwal, A., Boldrick, J., Sabet, H., Tran, T., Yu, X., Marti, G., Moore, T., J, H., Lu, L., Lewis, D., Tibshirani, R., Sherlock, G., Chan, W., Greiner, T., Weisenburger, D., Armitage, K., Levy, R., Wilson, W., Greve, M., Byrd, J., Botstein, D., Brown, P. & Staudt, L. (2000) *Nature* 403, 503-511.
2. Eisen, M., Spellman, P., Brown, P. & Botstein, D. (1998) *Proc. Natl. Acad. Sci. USA* 95, 14863-14868.
3. Weinstein, J., Myers, T., O'Connor, P., Friend, S., Fornace, A., Kohn, K., Fojo, T., Bates, S., Rubinstein, L., Anderson, N., Buolamwini, J., van Osdol, W., Monks, A., Scudiero, D., Sausville, E., Zaharevitz, D., Bunow, B., Viswanadhan, V., Johnson, G., Wittes, R. & Paull, K. (1997) *Science* 275, 343-349.

Cluster analysis works best for a large number of samples. Moreover, cluster analysis provides little information about statistical significance. To answer biologically important questions, a method is needed which can analyze a relatively small number of samples and provide a measure of statistical certainty. Methods based on conventional t-tests provide the probability (p) that a difference in gene expression occurred by chance. See for example, the following articles:

4. Roberts, C., Nelson, B., Marton, M., Stoughton, R., Meyer, M., Bennett, H., He, Y., Dai, H., Walker, W., Hughes, T., Tyers, M., Boone, C. & Friend, S. (2000) *Science* 287, 873-880.
5. Galitski, T., Saldanha, A., Styles, C., Lander, E. & Fink, G. (1999) *Science* 285, 251-254.

In conventional t tests, $p=0.01$ may be significant in the context of experiments designed to evaluate small numbers of genes. However, a microarray experiment for 10,000 genes would identify 100 genes by chance.

One approach for ascertaining the statistical significance of microarray data is known as the "fold change" method. In this approach, if one were interested in measuring the effects of radiation on gene expression, a number of biological samples are subjected to radiation, and their gene expression is then measured. Other biological samples are measured without being subjected to radiation. The "fold change" method identifies genes as having been changed significantly by the radiation if the ratio of the average gene expression measured after being subjected to the radiation to the gene expression measured without being subjected to radiation is greater than a certain threshold or less then another threshold. As further explained below, the "fold change" method, in some instances, yields unacceptably high false discovery rates.

In one attempt to improve on the "fold change" method, genes are identified to be significantly changed if a certain fold change is observed consistently between paired samples. While this yields a moderate improvement over the "fold change" method, this improved "pair wise fold change" method still yields a rather high false discovery rate.

As also noted above, conventional techniques analyze differences in gene expression levels, such as PM-MM, so that negative expression values are possible during analysis. Conventional methods of calculation and graphical representation employ log-log plots which do not permit negative values. Where linear plots are used instead for representing such possible negative values, it is found, however, that most of the values in the plots tend to congregate in a small area so that it is difficult to resolve them visually. It is, therefore, desirable to provide improved techniques for calculation and representation of data.

It is, therefore, desirable to provide an improved system for analyzing and representing data obtained from microarrays whereby the above-described difficulties are alleviated.

SUMMARY OF THE INVENTION

A new method, referred to herein as Significance Analysis of Microarrays (SAM), identifies genes with statistically significant differences in expression or other biological characteristics (such as gene copy number or levels of protein encoded by the genes), referred to below as values associated with the genes, by assimilating a set of gene-specific microarray data. For example, SAM may assign each gene a score representing such associated values, based on differences in gene expression or other biological characteristics in the data relative to the standard deviation of repeated measurements for that gene. Genes with scores greater than an adjustable threshold are deemed potentially significant. In some situations, gene expression may vary over a wide range of values, so that, in order to take full advantage of statistical analysis, it is preferable to choose statistical parameters for characterizing genes so that statistical significance can be assessed despite such variation of values. Preferably the parameters are chosen so that they are substantially independent of the ranges of values that characterize the genes. Thus, where a plurality of genes are associated with a plurality of sets of values obtained from data sources, a statistical parameter is provided that contains information concerning differences in the associated values of the genes among the sets. In one implementation, the parameters of the genes are adjusted so that the parameters are substantially independent of the average associated values of the genes over the sets. An observed value and an expected value of the adjusted parameter are calculated and compared to identify genes whose associated values differ by an amount of statistical significance among the sets. The sets of associated values of genes may be obtained from measurements using microarrays, data derived from such measurements, calculations or predictions using gene models, or other data sources.

As noted above, gene expression or other biological characteristics of genes may vary over a wide range of values. Therefore, for genes whose expression or other characteristics have high values, even a difference that is a small percentage of the high values may overshadow and mask larger relative differences for genes whose expression or other characteristics have lower values. Furthermore, factors inherent in the process of acquisition of the data analyzed may introduce noise that may mask changes or differences in gene expression, or cause genes to be erroneously identified as having changes of statistical significance. This problem can be alleviated by ranking the genes by their values of the parameter, and by deriving expected values of the parameter of different ranks. The expected value for the parameter for each rank is then compared with the value of the parameter of the gene of the same rank to identify genes that exhibit changes of statistical significance.

In one embodiment, the expected value for the parameter for each rank is obtained by permuting the associated values of genes, deriving a value of such parameter for each gene in each permutation, ranking the values of the parameter, and obtaining an average value of the parameter of each rank for the permutations.

Inherent in some statistical methods such as the one described above is that some genes may be erroneously identified as ones with statistically significant differences in expression or other characteristics. A good indication of the effectiveness of the method is to compute a false discovery rate for the method.

To estimate the percentage of such genes identified by chance (the false discovery rate, FDR), nonsense genes are identified by analyzing permutations of the measurements. The threshold score can be adjusted to identify smaller or larger sets of genes, and FDRs are calculated for each set.

The FDR may be found by permuting the associated values of genes, deriving a value of such parameter for each permutation, ranking the values of the parameter, and comparing the values of the parameter to a threshold to find the FDR. In one embodiment, this is implemented by counting the number of genes with parameter values that exceed a positive threshold or fall below a negative threshold. One possible method for estimating the FDR is to define FDR as the number of such nonsense genes divided by the number of actual genes with parameter values that exceed the positive threshold or fall below the negative threshold.

Where SAM is used in connection with data analysis of diseases, gene expression or other characteristic values may correlate with patient survival time. In such event, pairs of death and risk sets may be defined, each pair having a corresponding patient death time, where the death set includes associated values corresponding to the death time and the risk set includes values corresponding to times occurring after the death time. A parameter is then provided for each of the genes containing information concerning differences in the associated values of the gene among the sets. An observed and an expected value of the parameter for each gene are then derived and compared to identify genes that exhibit behavior of statistical significance.

To avoid the problem inherent in the conventional technique of using sharp thresholds in deriving representative values of genes, smooth weighting functions may be used to reduce distortion. In order to analyze and/or represent expression levels that may be negative or positive in value, odd root values may be analyzed and/or graphically displayed so that the values do not congregate in a small area in the plot, and this facilitates analysis and comparison.

The above-described features may be embodied as a program of instructions executable by computer to perform the above-described different aspects of the invention. Hence, any of the techniques described above may be performed by means of software components loaded into a computer or any other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or any other type of computer network. The above features embodied in one or more computer programs may be performed by one or more computers running such program(s).

Each of the inventive features described above may be used individually or in combination in different arrangements. All such combinations and variations are within the scope of the invention.

BRIEF DESCRIPTION OF THE DRAWINGS

FIG. 2A illustrates the relative difference between irradiated and unirradiated states, where the statistic $d(i)$ was computed from expression measurements partitioned between irradiated and unirradiated cells.

FIG. 2B illustrates the relative difference between cell lines 1 and 2, where the statistic $d(i)$ was computed from expression measurements partitioned between cell lines 1 and 2.

FIG. 2C illustrates the relative difference between hybridizations A and B, where the statistic $d(i)$ was computed from the permutation in which the expression measurements were partitioned between the equivalent hybridizations A and B.

FIGS. 2D, 2E, 2F illustrate the relative differences for three permutations of the data that were balanced between cell lines 1 and 2.

FIGS. 3A-3C illustrates a process for identification of genes with significant changes in expression.

FIGS. 4A-4C illustrate a process for comparison of SAM to conventional methods for analyzing microarrays.

For simplicity in description, identical components are labelled in the same numerals in this application.

DETAILED DESCRIPTION OF THE PREFERRED EMBODIMENTS

Because of its biological importance, SAM is applied to the transcriptional response of lymphoblastoid cells to ionizing radiation (IR). Although the data were obtained from oligonucleotide microarrays representing 6800 genes, SAM can also be applied to cDNA microarrays in a similar manner.

Materials and Methods Used in the Invention

Preparation of RNA. Lymphoblastoid cell lines GM14660 and GM08925 (Coriell Cell Repositories, Camden, N.J.) were seeded at $2.5\times10^5$ cells/ml and exposed to 5 Gy 24 hours later. RNA was isolated, labeled and hybridized to the HuGeneFL GeneChip® microarray according to manufacturer's protocols (Affymetrix, Santa Clara, Calif.).

Microarray hybridization. Each gene in the microarray was represented by 20 oligonucleotide pairs, each pair consisting of an oligonucleotide perfectly matched to the cDNA sequence and a second oligonucleotide containing a single base mismatch. Because gene expression was computed from differences in hybridization to the matched and mismatched probes, expression levels were sometimes reported by the GeneChip® Analysis Suite software as negative numbers. To compare data from different microarray hybridizations, a reference data set was constructed from the average expression for each gene over the 8 data sets. Gene expression for each hybridization was plotted against the reference data set in a cube root scatter plot and scaled by a linear fit to the data points. Data were then cubed to return values to the original scale.

Northern blot hybridization. Total RNA (15 µg) was resolved by agarose gel electrophoresis, transferred to a nylon membrane, and hybridized to specific DNA probes, which were prepared by PCR amplification.

Results of Applying the Invention to a Biological System

RNA was harvested from two wild type human lymphoblastoid cell lines, designated 1 and 2, growing in an unirradiated state U, or in an irradiated state I, 4 hr after exposure to a modest dose of 5 Gy of IR. RNA samples were labeled and divided into two identical aliquots for independent hybridizations, A and B. Thus, data was generated from eight hybridizations (U1A, U1B, U2A, U2B, I1A, I1B, I2A, I2B).

To assess reproducibility in the data, identical aliquots of an mRNA sample (U1A and U1B) were analyzed with two microarrays from the same manufacturing lot. A linear scatter plot for gene expression confirmed that the data was generally reproducible (FIG. 1A), but failed to resolve the vast majority of genes that are expressed at low levels. To better resolve these genes, we chose to display the data in a cube root scatter plot. This permitted the inclusion of negative levels of expression that are sometimes generated by the GeneChip® software. The cube root scatter plot (FIG. 1B) revealed three salient features: the large percentage of genes (24%) assigned negative levels of expression, the large percentage of genes with low levels of expression, and the low signal to noise ratio at low levels of expression.

Figure 1A:
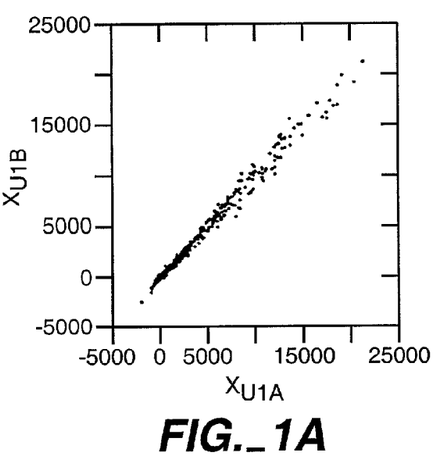
FIG. 1A is a linear scatter plot of gene expression in a sample hybridized to two microarrays using a conventional technique, where each gene (i) in the microarray is represented by a point with coordinates consisting of gene expression measured in uninduced cell line 1 from hybridization A, $x_{U1A}(i)$, and gene expression from the same cell line from hybridization B, $x_{U1B}(i)$.
Figure 1B:
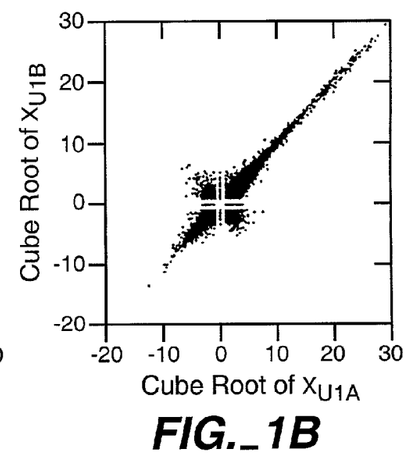
FIG. 1B is a cube root scatter plot of gene expression from the data in FIG. 1A to illustrate an aspect of the invention.

FIG. 1A is a linear scatter plot of gene expression in a sample hybridized to two microarrays using a conventional technique, where each gene (i) in the microarray is represented by a point with coordinates consisting of gene expression measured in uninduced cell line 1 from hybridization A, $x_{U1A}(i)$, and gene expression in the same cell line from hybridization B, $x_{U1B}(i)$. As can be observed from FIG. 1A, only a small number of highly expressed genes are resolved visually, with most of the genes compressed into a small region of the plot so that they would be difficult to resolve visually. One method of distributing such data points more uniformly is a logarithmic scatter plot, but the log function cannot accept the negative values for gene expression generated by the microarrays. FIG. 1B is a cube root scatter plot of gene expression from the data in FIG. 1A to illustrate an aspect of the invention. As will be clear from a comparison of FIGS. 1A, 1B, the genes with lower expression levels are more visually resolved in cube root plot of FIG. 1B compared to FIG. 1A. While cube root plots are illustrated herein, it will be understood that the fifth root or other odd root plots may be used instead and are within the scope of the invention.

Figure 1C:
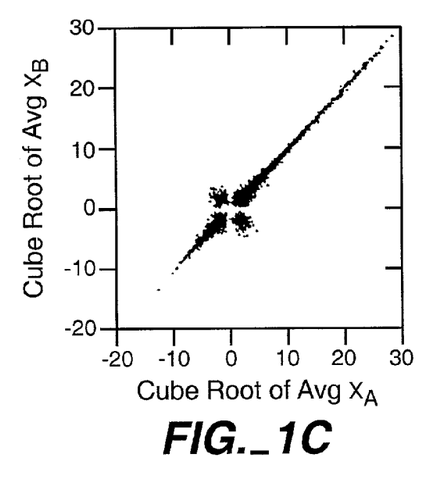
FIG. 1C is a cube root scatter plot of average gene expression (avg $x_A$) from the four A hybridizations (induced and uninduced, cell lines 1 and 2) and the four similar B hybridizations (avg $x_B$) to illustrate an aspect of the invention.

After scaling the data from different microarray hybridizations, a scatter plot was generated for average gene expression in the four A aliquots vs. the average in the four B aliquots, a partitioning of the data that eliminates biological changes in gene expression. The scatter was improved by averaging multiple data sets (compare FIGS. 1B and 1C). FIG. 1C is a cube root scatter plot of average gene expression from the four A hybridizations (avg $x_A$) and the four B hybridizations (avg $x_B$).

Figure 1D:
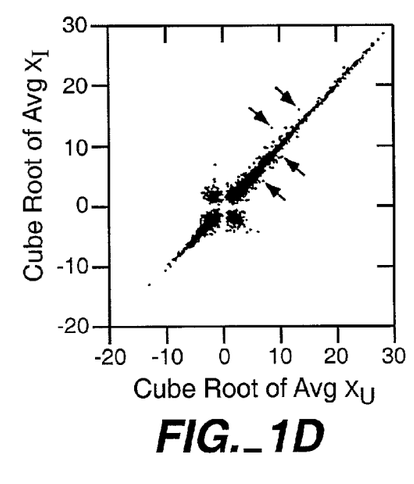
FIG. 1D is a cube root scatter plot of average gene expression from the four hybridizations with uninduced cells (avg $x_U$) and induced cells 4 hr after exposure to 5 Gy of IR (avg $x_I$), where some of the genes that responded to IR are indicated by arrows to illustrate an aspect of the invention.

To assess the biological effect of IR, a scatter plot was generated for average gene expression in the four irradiated states vs. the four unirradiated states (compare FIGS. 1C and 1D). FIG. 1D is a cube root scatter plot of average gene expression from the four hybridizations with uninduced cells (avg $x_U$) and induced cells 4 hr after exposure to 5 Gy of IR (avg $x_I$), where some of the genes that responded to IR are indicated by arrows to illustrate an aspect of the invention. A few of the potentially significant changes in gene expression are indicated by arrows in FIG. 1D, but the effect was not easily quantified, and it is desirable to provide a better method to identify changes with a level of statistical confidence.

The approach adopted herein was based on analysis of random fluctuations in the data. In general, the signal to noise ratio decreased with decreasing gene expression (FIGS. 1B-1D). However, even for a given level of expression, it is found that fluctuations were gene specific. To account for gene-specific fluctuations, a statistic is defined based on the ratio of change in gene expression to standard deviation in the data for that gene. The "relative difference" d(i) in gene expression is:

$$d(i)=[x_I(i)-x_U(i)]/[s(i)+s_0] \qquad (1)$$

where $x_I(i)$ and $x_U(i)$ are defined as the average levels of expression for gene (i) in states I and U, respectively. The "gene-specific scatter" s(i) is the standard deviation in the data:

$$s(i) = \left( \left\{ \sum_m [x_m(i) - x_I(i)]^2 + \sum_n [x_n(i) - x_U(i)]^2 \right\} \{1/n_1 + 1/n_2\}/\{n_1 + n_2 - 2\} \right)^{1/2} \qquad (2)$$

where $\Sigma_m$ and $\Sigma_n$ are summations of the expression measurements in states I and U, respectively, and $n_1$ and $n_2$ are the numbers of measurements in states I and U (4 in this experiment). A constant $s_0=3.3$ was chosen by minimizing the coefficient of variation of the standard deviation of d(i) as a function of s(i), thus permitting d(i) values to be compared among all genes in the microarray. While a relative difference parameter d(i) as set forth in equation (1) is preferable, it will be understood that other difference functions that depend on the differences between the associated values of the genes among the sets (e.g. set of measurements in state U and set of same in state I) and on scatter values among the sets may be used and are within the scope of the invention.

As noted above, factors inherent in the process of acquisition of microarray data itself may introduce noise that renders it difficult to discover the significance of differences in gene expression or other biological behavior or falsely identify genes to be of statistical significance. To overcome such problem, a number of methods are described above which allow full utilization of the microarray data. One difficulty in making use of the microarray data is due to the fact that the expression levels of the genes have a wide range of values or scattered values. It is, therefore, desirable to adjust the parameter d(i) so that it is essentially independent of the wide variation of the values of the parameter d(i) and/or of the scatter value s(i). After the parameter has been so adjusted, then all of the data can be fully utilized.

In one embodiment, the adjustment is accomplished by dividing the scatter values or average associated values of the genes into subsets each having a similar range of values. For example, the scatter values or average associated values of the genes may be divided into ten subsets in accordance with which percentile such values fall into. In other words, the first of the ten subsets will contain the top tenth percentile of the scatter values or average associated values of the genes, the second subset containing the second to the top tenth percentile of such values and so on. The standard deviation of the parameter d(i) is then calculated within each subset and a coefficient of variation of the standard deviations of the parameter values for the ten subsets is then minimized by varying the value of the constant $s_0$ appearing in equation 1. After the constant $s_0$ has been so adjusted, the parameter d(i) is then substantially independent of wide variations in scatter values or average associated values of the genes, so that all of the microarray data can be effectively used.

Figure 2A:
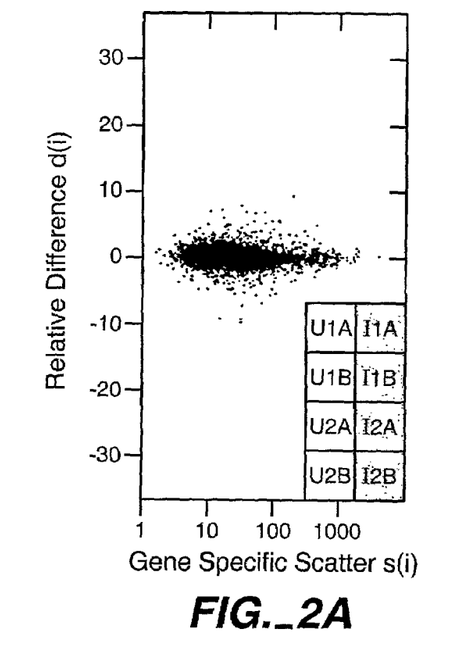
FIGS. 2A-2F are scatter plots of relative difference in gene expression $d(i)$ versus gene specific scatter $s(i)$, where the data were partitioned to calculate $d(i)$ as indicated by the bar codes, and where the shaded and unshaded entries were used for the first and second terms in the numerator of $d(i)$ in Equation 1 set forth below.
Figure 2B:
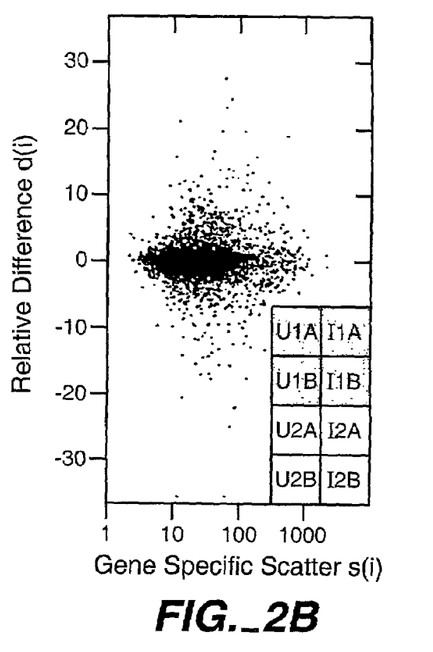

Scatter plots of d(i) vs. log[s(i)] are shown in FIGS. 2A-2F which are scatter plots of relative difference in gene expression d(i) versus gene specific scatter s(i), where the data were partitioned to calculate d(i) as indicated by the bar codes, and where the shaded and unshaded entries were used for the first and second terms in the numerator of d(i) in Equation 1 set forth below. FIG. 2A illustrates the relative difference between irradiated and unirradiated states, where the statistic d(i) was computed from expression measurements partitioned between irradiated and unirradiated cells. By contrast, the scatter plot for relative difference between cell lines 1 and 2 shows more marked changes in FIG. 2B, which illustrates the relative difference between cell lines 1 and 2. In FIG. 2B, the statistic d(i) was computed from expression measurements partitioned between cell lines 1 and 2. Thus, the relative difference between cell lines 1 and 2 appears to exceed that between irradiated and unirradiated states.

Figure 2C:
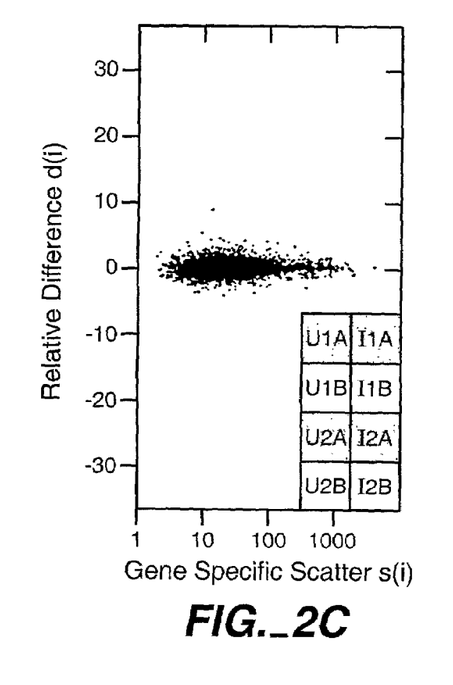

These relative differences exceeded random fluctuations in the data, as measured by the relative difference between hybridizations A and B in FIG. 2C which illustrates the relative difference between hybridizations A and B. In FIG. 2C, the statistic d(i) was computed from the permutation in which the expression measurements were partitioned between the equivalent hybridizations A and B.

Figure 2D:
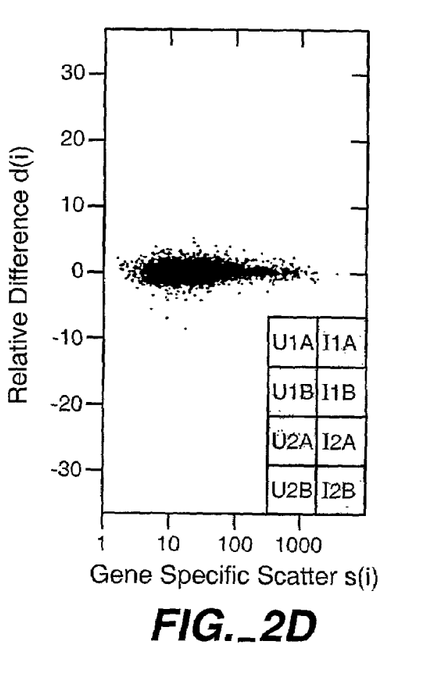
Figure 2E:
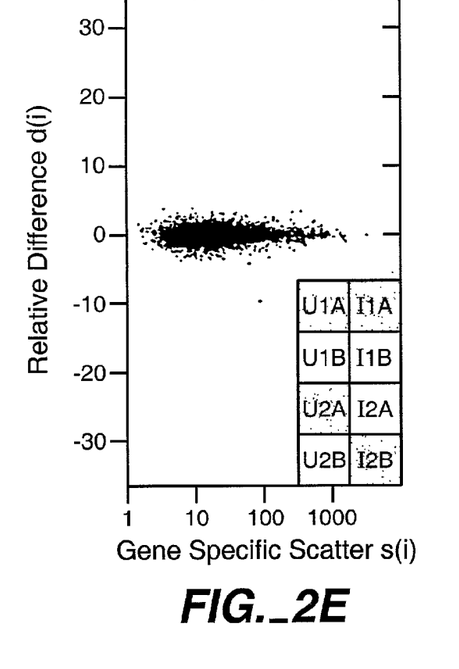
Figure 2F:
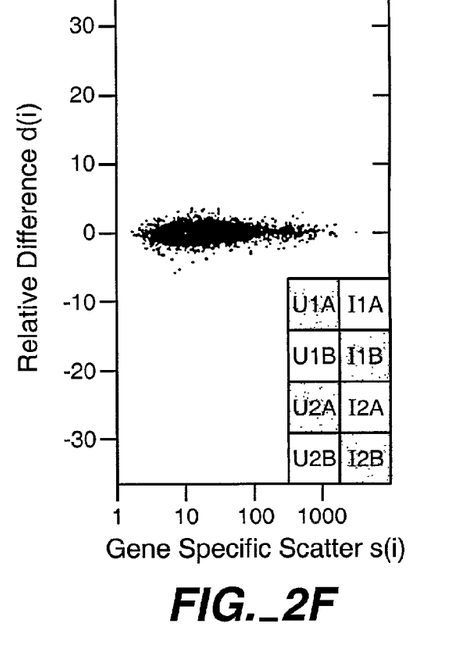

Although the relative difference computed from hybridizations A and B provided a control for random fluctuations, additional controls were desirable to assign statistical significance to the biological effect of IR. Instead of performing more experiments, which are expensive and labor-intensive, a large number of controls are generated by computing relative differences from permutations of the hybridizations for the 4 irradiated and 4 unirradiated states. To minimize potentially confounding effects from differences between the two cell lines, the data was analyzed using the 36 permutations that were balanced for cell lines 1 and 2. Permutations were defined as balanced when each group of four experiments contained two experiments from cell line 1 and two experiments from cell line 2. FIGS. 2D, 2E, 2F illustrate the relative differences for three permutations of the data that were balanced between cell lines 1 and 2.

Relative differences from random permutations of the hybridizations indicate noise inherent in the process of data acquisition. From the examples illustrated above, it is seen that relative differences stemming from the differences between cell lines may mask statistically significant changes in gene expression caused by radiation, so that for this reason, it may be preferable to use only data from balanced permutations, to reduce the effects on the statistics from differences between the cell lines.

Another control that can be exerted is by ranking the values of the relative difference parameter d(i) Although gene expression levels can vary widely, the relative difference d(i) is a measure of statistical significance substantially independent of expression level. As another control for assigning statistical significance, the largest relative differences from the 36 permutations may indicate noise from statistical fluctuations in the data. One may compute the average value of the largest relative differences from all 36 permutations. Thus, comparing the largest relative difference among all the genes to the largest relative differences from the permutations provides one possible test for identifying genes to be of statistical significance. Therefore, the average of the largest relative differences from the 36 permutations is the expected relative difference for such gene. A comparison of the relative difference of such gene with its expected value can be used as control as to whether statistical significance should be assigned to such gene. The same reasoning applies to the gene of the second highest relative difference and comparison to the second largest relative differences from the permutations, and so on for all the genes involved in the calculation.

In other words, to find significant changes in gene expression, genes were ranked by magnitude of their d(i) values, so that d(1) is the largest relative difference, d(2) is the second largest relative difference, and d(i) is the $i^{th}$ largest relative difference, or the ith rank. For each of the 36 balanced permutations, relative differences $d_p(i)$ are also calculated, and the genes are again ranked such that $d_p(i)$ was the $i^{th}$ largest relative difference for permutation p. The expected $d_E(i)$ was defined as the average over the 36 balanced permutations, $$d_E(i)=\Sigma_p d_p(i)/36 \qquad (3)$$

Figure 3A:
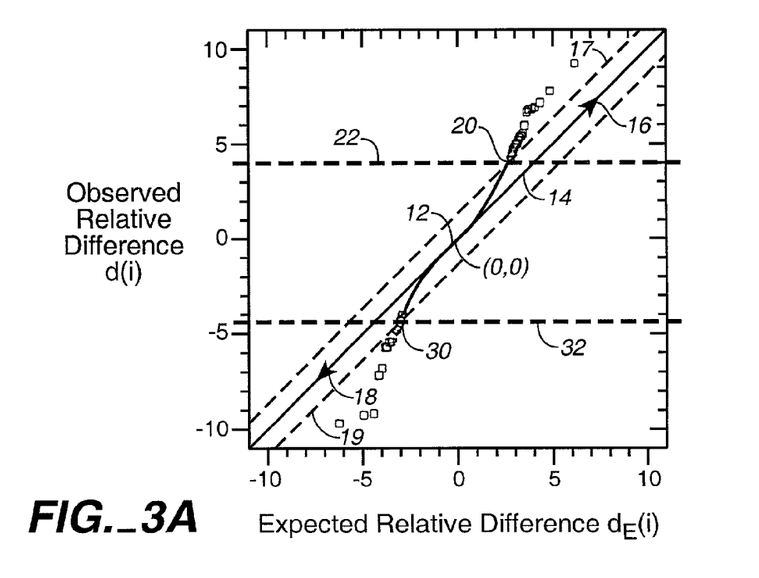
FIG. 3A is a scatter plot of the observed relative difference $d(i)$ versus the expected relative difference $d_E(i)$, where the solid line at 45 degrees indicates the line for $d(i)=d_E(i)$, where the observed relative difference is identical to the expected relative difference, and where the dotted lines are drawn at a distance $\Delta=1.2$ from the solid line.
Figure 3B:
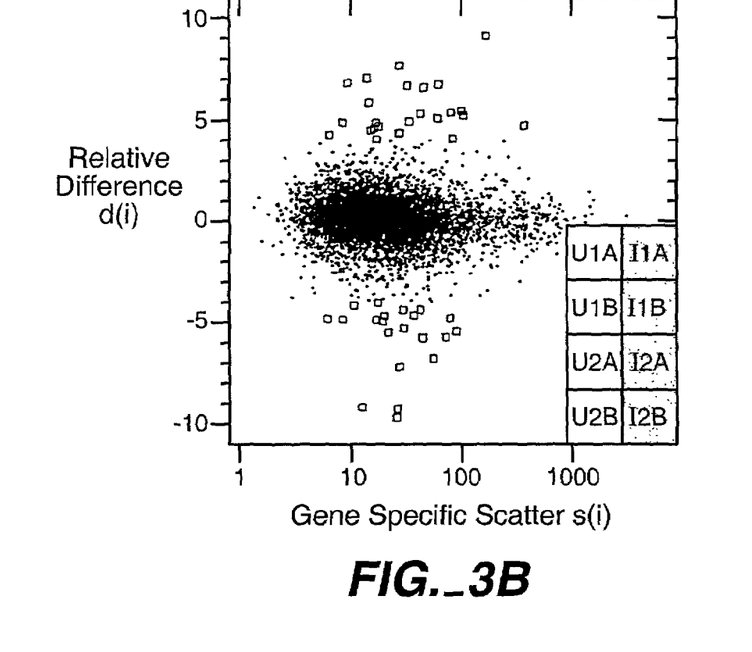
FIG. 3B is scatter plot of $d(i)$ versus scatter $s(i)$.
Figure 3C:
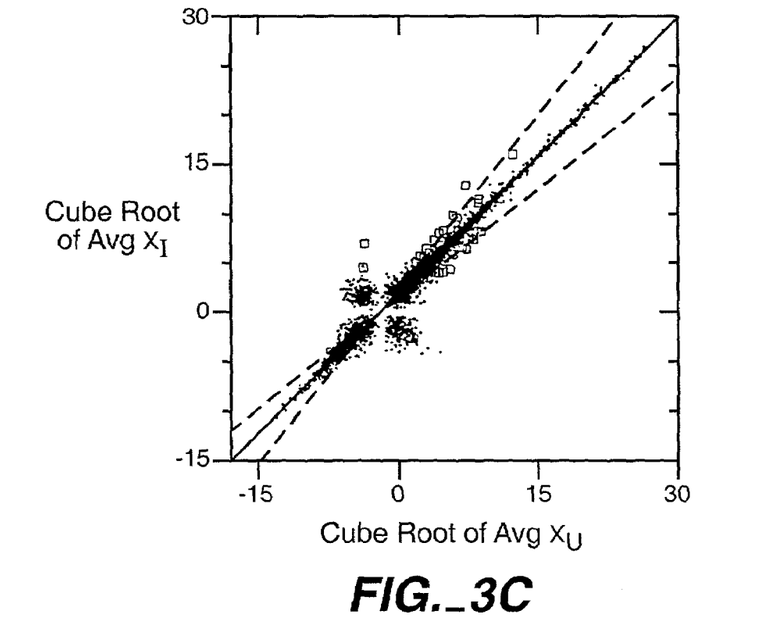
FIG. 3C is a cube root scatter plot of average gene expression in induced and uninduced cells, where the cutoffs for 2-fold induction and repression are indicated by the dashed lines, and where in all panels, the 46 potentially significant genes for $\Delta=1.2$ are indicated by the squares.

FIGS. 3A-3C illustrates a process for identification of genes with significant changes in expression. FIG. 3A is a scatter plot of the observed relative difference d(i) versus the expected relative difference $d_E(i)$, in which the solid line indicates the line for d(i)=$d_E(i)$, where the observed relative difference is identical to the expected relative difference, and in which the dotted lines are drawn at a distance Δ=1.2 from the solid line. FIG. 3B is a scatter plot of d(i) versus scatter s(i). FIG. 3C is a cube root scatter plot of average gene expression in induced and uninduced cells, where the cutoffs for 2-fold induction and repression are indicated by the dashed lines, and where in all panels, the 46 potentially significant genes for Δ=1.2 are indicated by the squares.

To identify potentially significant changes in expression, a scatter plot of the observed relative difference d(i) vs. the expected relative difference $d_E(i)$ (FIG. 3A) is used. For the vast majority of genes, d(i)≅$d_E(i)$. However, some genes are represented by points displaced from the d(i)=$d_E(i)$ line by a distance greater than a threshold Δ. For example, the threshold Δ=1.2 illustrated by the broken lines in FIG. 3A yielded 46 genes that were "called significant." These 46 genes are shown in the context of the scatter plot for d(i) vs. log[s(i)] (FIG. 3B) and in the scatter plot for the cube root of gene expression $x_I(i)$ vs. $x_U(i)$ (FIG. 3C). Clearly, genes identified by d(i) do not necessarily have the largest changes in gene expression.

As noted above, the relative differences of the various permutations indicate noise inherent in the data acquisition process. Such relative differences may then be used to determine the number of genes falsely identified to be of statistical significance. False discovery rate may be found by comparing such relative differences to thresholds. FIG. 3A may be used for such purposes as well, where the "observed" relative difference d(i) in the figure is one obtained from permutations as described below.

In one embodiment, to determine the number of falsely significant genes generated by SAM, horizontal cutoffs were defined as the smallest d(i) among the genes called significantly induced and the least negative d(i) among the genes called significantly repressed. The number of falsely significant genes corresponding to each permutation was computed by counting the number of genes that exceeded the horizontal cutoffs for induced and repressed genes. The estimated number of falsely significant genes was the average of the number of genes called significant from all 36 permutations. Table 1, attached hereto as appendix A and made part of this application, shows the results for different values of Δ. For Δ=1.2, the permuted data sets generated an average of 8.4 falsely significant genes, compared to 46 genes called significant, yielding an estimated FDR of 18%. As Δ decreased, the number of genes called significant by SAM increased, but at the cost of an increasing FDR. (Omitting $s_0$ from Equation 1 produced higher FDRs of 45%, 35%, and 28% for Δ=0.6, 0.9, and 1.2.).

Thus, as illustrated in FIG. 3A, the "observed" relative difference d(i) is plotted against expected relative difference $d_E(i)$ for all of the 36 permutations. To arrive at the plot in FIG. 3A, both the "observed" and the expected relative differences are computed using the associated values of the genes in the 36 permutations using equations (1)-(3) above.

One then proceeds from the point 12 (at coordinates (0,0)) in the plot and proceed along line 14 at 45° to the axis in the positive direction along arrow 16. When the smallest positive "observed" relative difference d(i) is encountered that exceeds the expected relative difference $d_E(i)$ by a set threshold defined by dotted line 17, such as at point 20, such value of the d(i) is then set as a horizontal threshold. This value of d(i) then becomes a horizontal cutoff 22, so that the number of genes with positive "observed" relative difference values exceeding such threshold 22 from the 36 permutations compared to the unpermitted data would provide an indication of the false discovery rate for induced genes. This accounts for the falsely significant genes that are induced.

To discover the falsely significant genes that are repressed, one would then proceed again from point 12 along line 14 but along the negative direction 18 until one again encounters at point 30 the least negative observed relative difference d(i) that exceeds the expected relative difference $d_E(i)$ by a set threshold indicated by dotted line 19. Such smallest negative d(i) is then set as the negative horizontal cutoff threshold 32. The genes whose negative relative differences are more negative than such horizontal cutoff 32 from the permitted and unpermitted data are used to estimate the FDR.

To test the above described method for determining the FDR, artificial data sets are constructed in which a subset of genes was induced over a background of noise. When SAM was used to analyze such data sets, the estimated FDR accurately predicted the correct number of falsely significant genes.

The above method for setting thresholds provides asymmetric cutoffs for induced and repressed genes. In other words, the magnitudes of the two horizontal cutoffs 22, 32 need not be the same. The alternative is the standard t-test, which imposes a symmetric horizontal cutoff, with a d(i)>c for induced genes and a d(i)<−c for repressed genes. However, the asymmetric cutoff is preferred because it allows for the possibility that d(i) for induced and repressed genes may behave differently in some biological experiments.

Figure 4A:
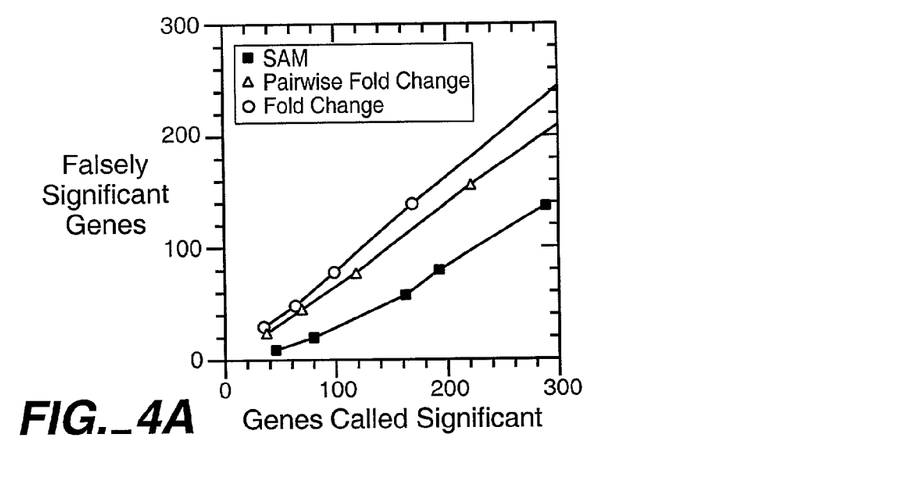
FIG. 4A illustrates falsely significant genes plotted against number of genes called significant, where of the 57 genes most highly ranked by the fold change method, 5 were included among the 46 genes most highly ranked by SAM.

FIGS. 4A-4C illustrate a process for comparison of SAM to conventional methods for analyzing microarrays. FIG. 4A illustrate falsely significant genes plotted against number of genes called significant, where of the 57 genes most highly ranked by the fold change method, 5 were included among the 46 genes most highly ranked by SAM. Of the 38 genes most highly ranked by the pairwise fold change method, 11 were included among the 46 genes most highly ranked by SAM. These results were consistent with the FDRs of SAM compared to the fold change and pairwise fold change methods.

Figure 4B:
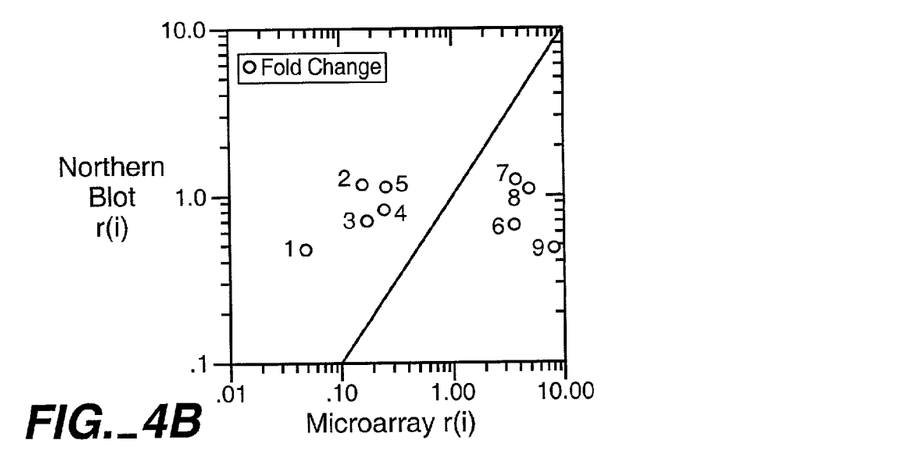
FIG. 4B is a Northern blot validation for genes identified by the fold change method, where values of $r(i)$ are plotted for genes chosen at random from the 57 genes most highly ranked by the fold change method.

FIG. 4B is a Northern blot validation for genes identified by the fold change method, where values of r(i) are plotted for genes chosen at random from the 57 genes most highly ranked by the fold change method. The genes are: cyclin F (1); parathymosin (2); N-acetyl glucosaminyltransferase (3); eIF-4 gamma (4); dynamin (5); interferon consensus sequence binding protein (6); heart muscle specific protein DRAL/SLIM3/FHL-2 (7), U1 snRNP-specific C protein (8); and maxi K potassium channel beta subunit (9).

Figure 4C:
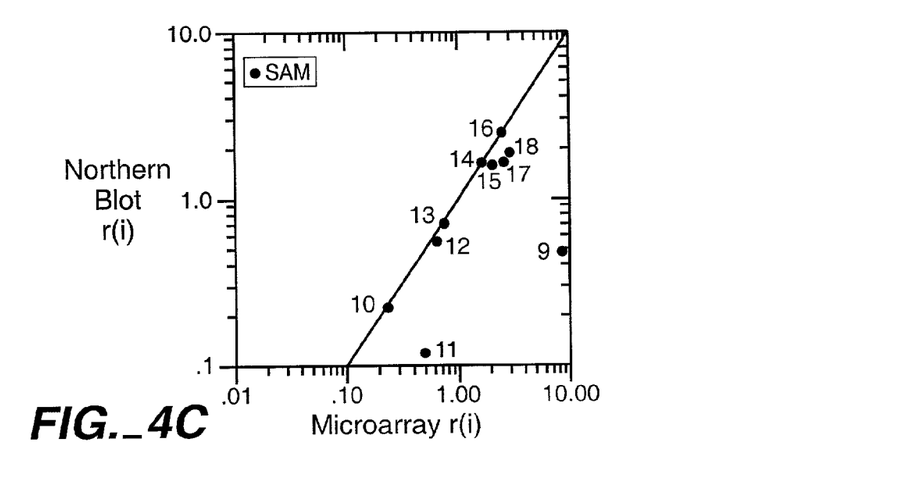
FIG. 4C is a Northern blot validation for genes identified by SAM, where results are plotted for genes chosen at random from the 46 genes most highly ranked by SAM. The straight lines in FIGS. 4B and 4C indicate the position of exact agreement between Northern blot and microarray results.

FIG. 4C is a Northern blot validation for genes identified by SAM, where results are plotted for genes chosen at random from the 46 genes most highly ranked by SAM: maxi K potassium channel beta subunit (9); cyclin B (10); PLK (11); ckshs2 (12); IL2 receptor beta chain (13); PTP (CAAX1) (14); p48 (15); XPC (16); Fas (17); and mdm2 (18).

SAM proved to be superior to conventional methods for analyzing microarrays (Table 1 and FIG. 4A). First, SAM was compared to the approach of identifying genes as significantly changed if an R-fold change was observed. In this "fold change" method, $r(i)=x_I(i)/x_U(i)$, and gene (i) was called significantly changed if r(i)>R or r(i)<1/R. To permit computation of r(i) from negative values for gene expression, $x_I(i)$ and $x_U(i)$ were converted to 10 when their values were negative or less than 10. The results of this procedure yielded unacceptably high FDRs of 73% to 84%.

Another approach attempts to account for uncertainty in the data by identifying genes as significantly changed if an R-fold change is observed consistently between paired samples (7). To apply this "pairwise fold change" method to our 4 data sets before and 4 data sets after IR, changes in gene expression were declared significant if 12 of 16 pairings satisfied the criteria r(i)>R or r(i)<1/R. Despite the demand for consistent changes between paired samples, this method yielded FDRs of 60% to 71%.

To understand why fold-change methods fail, note that the vast majority of genes are expressed at low levels where the signal to noise ratio is very low (FIG. 3C). Thus, 2-fold changes in gene expression occur at random for a large number of genes. Conversely, for higher levels of expression, smaller changes in gene expression may be real, but these changes are rejected by fold-change methods. The pairwise fold change method provides modest improvement and remained inferior to SAM.

Of the 46 genes most highly ranked by SAM ($\Delta=1.2$), 36 increased or decreased at least 1.5-fold with $r(i)\geq 1.5$ or $r(i)\leq 0.67$. The number of falsely significant genes that met these two criteria was 4.5, corresponding to a FDR of 12%. Fas was identified 3 times as alternately spliced forms, leaving 34 independent genes. As an indication of biological validity, 10 of the 34 genes have been reported in the literature as part of the transcriptional response to IR. TNF-α was reported to be induced by others under different conditions (8) but was repressed here. We validated our microarray result by Taq-Man PCR.

To test the validity of SAM directly, Northern blots were performed for genes that were randomly selected from the 46 and 57 genes most highly ranked by SAM ($\Delta=1.2$) and the fold change method (at least 3.6-fold change), respectively. Northern blots showed little correlation with the genes identified by the fold change method (FIG. 4B), but strong correlation with the genes identified by SAM (FIG. 4C). Indeed, Northern blots contradicted only 1 of 10 genes identified by SAM, consistent with our estimated FDR.

Nineteen of the 34 genes most highly ranked by SAM appear to be involved in the cell cycle. Three are known to be induced in a p53-dependent manner: p21, cyclin G1, and mdm2 (9-11). Six cell cycle genes were repressed: ubiquitin carrier protein E2-EPF, p55cdc, cyclin B, ckshs2, cdc25 phosphatase, and wee1 kinase (12, 13). Five genes encoding the mitotic machinery were also repressed: PLK kinase, mitotic kinesin-like protein 1 (MKLP-1), mitotic centromere-associated kinesin (MCAK), cdc25 associated protein kinase (CTAK1), and the kinetocore motor CENP-E (14-16). Four genes involved in cell proliferation were induced or repressed: the farnesylated protein tyrosine phosphatase PTP(CAAX1), OX40 ligand, lymphocyte phosphatase associated phosphoprotein (LPAP), and c-myc (17-21). Some responses were paradoxical. For example, cdc25 phosphatase and wee1 kinase have antagonistic effects on the phosphorylation state of cdc2, but both genes were repressed. Repression of these genes together with the mitotic genes may represent a damage response that dismantles the cell cycle machinery until the cell has repaired the damaged DNA.

Four of the 34 genes play roles in DNA repair, but none are involved in the repair of IR-induced double-strand breaks. Instead, the genes (p48, XPC, gadd45, PCNA) have roles in nucleotide excision repair, a pathway conventionally associated with UV-induced damage (22-25). We confirmed the induction of these genes by Northern blot (26-28). Fornace et al. reported defective removal of base damage induced by IR in xeroderma pigmentosum cells (29). Leadon et al. reported that a novel DNA repair pathway involving long excision repair patches of at least 150 nucleotides is activated by IR, but not UV (30). Our results suggest that this novel pathway might include p48, XPC, gadd45, and PCNA.

Three of the 34 genes play roles in apoptosis (Fas, bcl-2 binding component 3, TNF-α). The remaining genes may have previously unsuspected roles in the DNA damage response, or may be among the estimated set of four falsely detected genes. Attached hereto as Appendix B and made a part of this application is Table 2, which sets forth the genes with changes in expression called significant by SAM.

Discussion

The 34 genes most highly ranked by SAM are only a subset of all the genes that change 1.5-fold with IR. The difference between the number of genes called significant and the number of falsely significant genes was calculated for decreasing values of Δ=0.3, 0.2 and 0.1, and found the difference to be 92, 170, and 184 respectively. Thus SAM suggests that at least 180 genes are induced or repressed by 5 Gy IR.

In conclusion, SAM successfully identified those genes on a microarray with bona fide changes in expression. Here, SAM found genes whose expression changed between two states. SAM can also be generalized to other types of experiments by expressing d(i) in other ways. Suppose the data includes gene expression $x_j(i)$ and a response parameter $y_j$, in which i=1, 2, . . . , m genes, j=1, 2, . . . , n samples. The generalized statistical parameter still takes the form $d(i)=r(i)/[s(i)+s_0]$. Only the definitions of r(i) and s(i) change. For example, r(i) can be correlated with factors other than irradiation, such as different type of tumors or survival time, as described in more detail below, where r(i) simply indicates relative differences in associated values, not necessarily those caused by changes due to radiation.

To identify genes whose expression is specifically different in a subset of a set of samples, the parameter d(i) is defined in terms of the Fisher's linear discriminant. One goal might be to identify genes whose expression in one type of tumor is different from its expression in other types of tumors. Suppose that a set of n samples consists of K non-overlapping subsets, with $y_j \in \{1, \ldots, K\}$. Define $C(k)=\{j:y_j=k\}$. Let $n_k$=number of observations in C(k). The average gene expression in each subset is $\underline{x}_k(i)=\Sigma_{j \in C(k)} x_j(i)/n_k$ and the average gene expression for all n samples is $\underline{x}(i)=\Sigma_j x_j(i)/n$. Then define:

$$r(i)=\{[\Sigma_k n_k/\Pi_k n_k[\underline{x}_k(i)-\underline{x}(i)]^2\}^{1/2} \quad (4)$$

$$s(i)= \left\{\left[\sum_k (1/n_k)\Big/\sum_k (n_k-1)\right]\sum_k\sum_{j \in C(k)}[x_j(i)-\underline{x}_k(i)]^2\right\}^{1/2} \quad (5)$$

The quantity r(i) in equation 4 is the variance between subsets, and the quantity s(i) in equation 5 the sum of variances within each subset. Each subset may be data collected from a type of tumor. Thus a large value for the generalized statistical parameter d(i) indicates a difference in gene expression between subsets, or between the different types of tumors. The value of $s_0$ in d(i) is adjusted in a manner similar to that above by permuting the parameter k among the tumor subsets.

Thus, in general, where the associated values in each set can be classified into two or more subsets with values in each subset having a correlation with one another, a parameter may be selected using a quantity related to variances between the associated values in the subsets of the sets and the variances of the associated values within such subset of the sets. The quantity may relate to the sum of the variances between the associated values and the subsets of the sets and the sum or variances of the associated values within each subset of the sets.

To identify genes whose expression correlates with survival time, d(i) is defined in terms of the Cox's proportional hazards function. Express the response data in the form $y_j=(t_j, \delta_j)$. Here, $t_j$=survival time for patient (j) or censored survival time if the patient is still alive or lost to follow-up, and $\delta_j$=0 or 1, depending on whether patient (j) was censored ($\delta_j$=0) or died with a known survival time $t_j$ ($\delta_j$=1). Assume that there are K unique death times $z_1, z_2, \ldots, z_K$. Let D(k), for k=1, . . . , K be death sets D(k)=$\{i:t_1=z_k\}$. Let R(k) be risk sets R(k)=$\{i:t_1 \geq z_k\}$. Let $m_k$=number of patients in R(k). Let $d_k$=number of deaths at time $z_k$. The average expression of gene (i) in death set D(k) is: $x_k^*(i)=\Sigma_{j \in D(k)} x_j(i)/d_k$. The average expression of gene (i) in risk set R(k) is: $\underline{x}_k(i)=\Sigma_{j \in R(k)} x_j(i)/m_k$. Then define:

$$r(i)=\Sigma_k d_k[x_k^*(i)-\underline{x}_k(i)] \quad (6)$$

$$s(i)=\{\Sigma_k(d_k/m_k)\Sigma_{j \in R(k)}[x_j(i)-\underline{x}_k(i)]^2\}^{1/2} \quad (7)$$

SAM can be adapted for still other types of experimental data. For example, to identify genes whose expression correlates with a quantitative parameter, such as tumor stage, d(i) can be defined in terms of the Pearson correlation coefficient, as described in more detail in the example below.

A method for identifying genes whose expression correlates with a continuous parameter would be one identifying genes whose expression in a tumor correlates with survival time of the patient with the tumor.

Let $x_k(i)$ be the expression of gene (i) in sample (k) (e.g., the kth tumor). Define $\underline{x}(i)$ to be the average expression of gene (i) over all the samples.

Let $y_k$ be the value for the continuous parameter (e.g., time) associated with sample (k). Define $\underline{y}$ to be the average of the continuous parameter over all the samples.

The Pearson correlation coefficient, r(i) for gene (i) is:

$$r(i) = \sum_k [x_k(i)-\underline{x}(i)][y_k-\underline{y}] \Big/ \left[\sum_k [x_k(i)-\underline{x}(i)]^2 \sum_k (y_k-\underline{y})^2\right]^{1/2} \quad (8)$$

The values for r(i) are less than +1 and greater than −1. For r(i)≈+1, the corrleation is strongly positive. For r(i)≈−1, the correlation is strongly negative. An example of a modified Pearson correlation coefficient that could serve as the parameter d(i) is:

$$d(i) = \sum_k [x_k(i)-\underline{x}(i)][y_k-\underline{y}] \Big/ \quad (9)$$

-continued $$\left\{\left[\sum_k [x_k(i)-\underline{x}(i)]^2 \sum_k (y_k-\underline{y})^2\right]^{1/2} + s_o\right\}$$

The value of $s_O$ would be adjusted in the manner described above, thus permitting comparison across the entire set of genes. To compute the expected d(i), the survival times are permuted among the tumors.

In addition to applications using the Pearson correlation coefficient, another example includes the definition of d(i) for paired data, such as gene expression in tumors before and after chemotherapy. In each case, the FDR is estimated by random permutation of the data for gene expression among the different experimental arms, i.e., permutations among the n arms of $y_j$.

Weighting Function to Improve Data Reproducibility

Figure 5A:
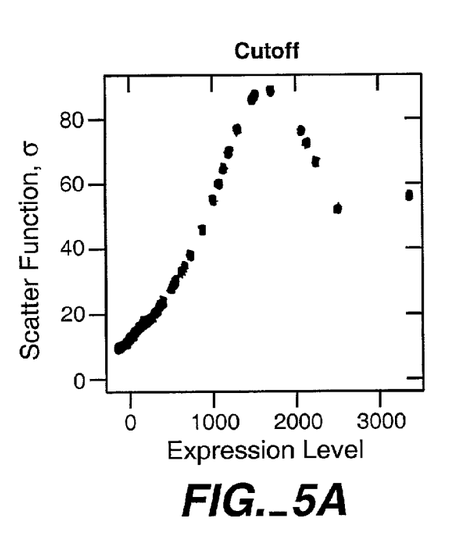
FIG. 5A is a graphical plot of a scatter function to illustrate effects of a conventional technique for processing gene expression which eliminates contributions from probes that diverge from a mean value by a predetermined cutoff.

For microarrays that contain several probes for each gene, expression is typically computed as a simple mean or a trimmed mean, which eliminates contributions from probes that diverge from the mean by a predetermined cutoff. Such methods fail to eliminate uncertainty in the data arising from probes that do not behave appropriately as shown in FIG. 5A.

Figure 5B:
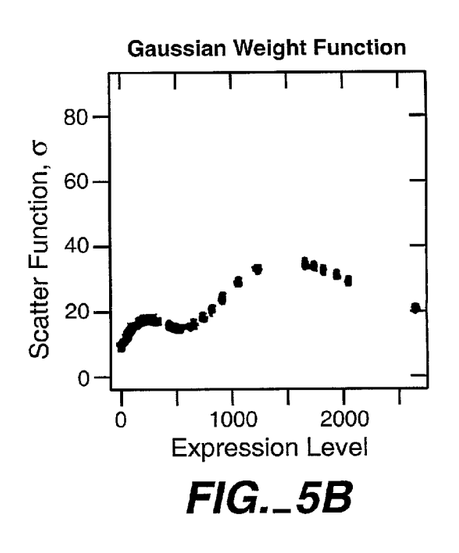
FIG. 5B is a graphical plot of a scatter function to illustrate effects of the use of a Gaussian weighting function for processing gene expression to illustrate an aspect of the invention.

Data reproducibility can be improved by modifying the contribution of each probe by a continuous weighting function. For example, the weight for probe (i) of a given gene can be determined by a Guassian weight function, $$w(i)=exp[-(x_1-x_0)^2/a^2] \quad (10)$$

where $x_0$=mean or median of data from all the probes for the gene, a=constant multiplied by standard deviation or median absolute deviation of data. When the Gaussian weight function was applied to an experiment in which the same sample was hybridized twice to two microarrays, there was major improvement in the data (FIG. 5B). The scatter function decreased by more than a factor of two and the number of negatively expressed genes decreased from 25% to 0.001%.

Thus, SAM is a robust and straightforward method that can be adapted to a broad range of experimental situations. SAM and its modifications are available for use on the world wide web at statclass.stanford.edu/SAM/SAMServlet. This web site is used at Stanford University.

Software Implementation

The invention has been described above, employing methods and producing plots as illustrated in the Figures. Such methods and graphs or plots may be produced with the aid of machines such as computers. Therefore, another aspect of the invention involves the software components that are loaded to a computer to perform the above-described functions. These functions provide results with the different advantages outlined above. The software or program components may be installed in a computer in a variety of ways.

As will be understood in the art, the inventive software components may be embodied in a fixed media program component containing logic instructions and/or data that when loaded into an appropriately configured computing device to cause that device to perform according to the invention. As will be understood in the art, a fixed media program may be delivered to a user on a fixed media for loading in a users computer or a fixed media program can reside on a remote server that a user accesses through a communication medium in order to download a program component. Thus another aspect of the invention involves transmitting, or causing to be transmitted, the program component to a user where the component, when downloaded into the user's device, can perform any one or more of the functions described above.

Figure 6:
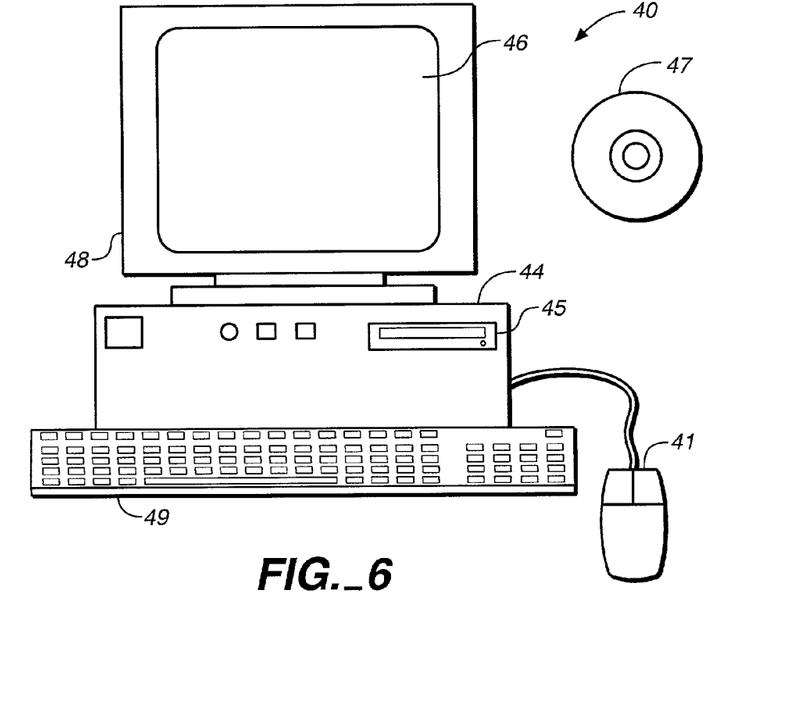
FIG. 6 is a block diagram showing a representative sample logic device in which aspects of the present invention may be embodied.

FIG. 6 shows an information appliance (or digital device) 40 that may be understood as a logical apparatus that can read instructions from media 47 and/or network port 49. Apparatus 40 can thereafter use those instructions to direct server or client logic, as understood in the art, to embody aspects of the invention. One type of logical apparatus that may embody the invention is a computer system as illustrated in 40, containing CPU 44, optional input devices 49 and 41, disk drives 45 and optional monitor 46. Fixed media 47 may be used to program such a system and may represent a disk-type optical or magnetic media, magnetic tape, solid state memory, etc. One or more aspects of the invention may be embodied in whole or in part as software recorded on this fixed media. Communication port 49 may also be used to initially receive instructions that are used to program such a system to perform any one or more of the above-described functions and may represent any type of communication connection, such as to the internet or any other computer network. The instructions or program may be transmitted directly to a user's device or be placed on a network, such as a website of the internet to be accessible through a user's device. All such methods of making the program or software component available to users are known to those in the art and will not be described here.

The invention also may be embodied in whole or in part within the circuitry of an application specific integrated circuit (ASIC) or a programmable logic device (PLD). In such a case, the invention may be embodied in a computer understandable descriptor language which may be used to create an ASIC or PLD that operates as herein described.

While the invention has been described above by reference to various embodiments, it will be understood that changes and modifications may be made without departing from the scope of the invention, which is to be defined only by the appended claims and their equivalents. All references referred to herein are incorporated by reference in their entireties.

TABLE 1

Comparison of methods for identifying changes in gene expression. To increase the stringency for calling significant changes in gene expression, parameters for each method (Δ and R) were increased, as described in the text. The number of falsely significant genes was estimated by permutation of the data sets. The false discovery rate (FDR) was defined as the percentage of falsely significant genes compared to the genes called significant.

| Method | Genes falsely significant | Genes called significant | FDR |
|---|---|---|---|
| SAM | | | |
| Δ = 0.4 | 134.9 | 288 | 47% |
| Δ = 0.5 | 78.1 | 192 | 41% |
| Δ = 0.6 | 56.1 | 162 | 35% |
| Δ = 0.9 | 19.1 | 80 | 24% |
| Δ = 1.2 | 8.4 | 46 | 18% |
| Fold change | | | |
| R = 2.0 | 283.1 | 348 | 81% |
| R = 2.5 | 137.8 | 169 | 82% |
| R = 3.0 | 76.8 | 99 | 78% |
| R = 3.5 | 46.7 | 64 | 73% |
| R = 4.0 | 29.3 | 35 | 84% |
| Pairwise fold change | | | |
| R = 1.2 | 245.6 | 355 | 69% |
| R = 1.3 | 155.4 | 220 | 71% |
| R = 1.5 | 76.2 | 118 | 65% |
| R = 1.7 | 44.8 | 70 | 64% |
| R = 2.0 | 22.8 | 38 | 60% |

TABLE 2

Genes with changes in expression called significant by SAM.

| Rank | Accession | d(i) | r(i) | s(i) | $x_U(i)$ | $x_I(i)$ | Gene |
|---|---|---|---|---|---|---|---|
| INDUCED GENES | | | | | | | |
| 1 | U09579† | 9.2 | 3.4 | 158 | 633 | 2119 | p21 |
| 2 | X83490† | 7.7 | 2.5 | 26 | 155 | 381 | Fas (alternate splice deleting exons 3 & 4) |
| 3 | U47621 | 7.1 | 2.9 | 13 | 61 | 178 | No55 nucleolar autoantigen |
| 4 | U18300† | 6.9 | 1.9 | 59 | 448 | 869 | p48, xeroderma pigmentosum group E gene |
| 5 | U48296 | 6.7 | 1.6 | 30 | 354 | 583 | protein tyrosine phosphatase PTP(CAAX1 |
| 6 | X63717† | 6.6 | 2.2 | 43 | 254 | 561 | Fas |
| 7 | D21089 | 5.5 | 2.4 | 96 | 392 | 930 | XPC, xeroderma pigmentosum group C gen |
| 8 | U39400 | 5.4 | 1.7 | 41 | 349 | 581 | NOF1 |
| 9 | X77794† | 5.3 | 1.6 | 99 | 964 | 1499 | cyclin GI |
| 10 | M60974† | 5.1 | 2.5 | 58 | 203 | 516 | gadd45 |
| 11 | D90224 | 4.9 | 2.8 | 32 | 96 | 270 | OX40 ligand, TNF ligand superfamily |
| 12 | U25138 | 4.9 | 9.0* | 16 | -4 | 90 | maxi K potassium channel beta subunit |
| 13 | J05614† | 4.8 | 1.7 | 352 | 2358 | 4043 | PCNA, proliferating cell nuclear antigen |
| 14 | X83492† | 4.8 | 1.8 | 17 | 117 | 213 | Fas (alternate splice deleting exons 4 & 7) |
| 15 | X85116 | 4.5 | 2.0 | 15 | 83 | 163 | EPB72, integral membrane protein |
| 16 | U50136 | 4.4 | 1.6 | 26 | 231 | 359 | leukotriene C4 synthase (LTC4S) |
| 17 | U82987 | 4.2 | 33.6* | 161 | -4 | 336 | bcl-2 binding component 3 (bbc3) |
| 18 | M92424† | 4.0 | 2.8 | 16 | 45 | 125 | mdm2 |
| REPRESSED GENES | | | | | | | |
| 1 | U01038 | -9.8 | 0.50 | 25 | 551 | 275 | PLK, polo kinase homolog |
| 2 | M91670 | -9.3 | 0.61 | 25 | 693 | 425 | ubiquitin carrier protein (E2-EPF) |
| 3 | U68233 | -9.3 | 0.48 | 12 | 275 | 133 | HRR-1 farnesol receptor |
| 4 | U05340 | -6.9 | 0.39 | 54 | 642 | 253 | p55cdc: present in dividing cells |
| 5 | M25753† | -5.8 | 0.23 | 43 | 345 | 78 | cyclin B |
| 6 | X97267 | -5.8 | 0.49 | 69 | 818 | 400 | lymphocyte phosphatase assoc phosphopro |
| 7 | S78187† | -5.5 | 0.63 | 20 | 357 | 224 | cdc25 phosphatase |
| 8 | X54942 | -5.5 | 0.52 | 87 | 1026 | 534 | ckshs2, cks1 protein homolog |
| 9 | U63743 | -5.0 | 0.59 | 19 | 265 | 158 | MCAK, mitotic centromere-associated kin |
| 10 | D86973 | -4.9 | 0.64 | 16 | 264 | 168 | GCN1, translational regulator of GCN4 |
| 11 | X62048† | -4.9 | 0.44 | 8 | 99 | 43 | wee1 kinase |
| 12 | M80359 | -4.9 | 0.40* | 6 | 25 | -19 | C-TAKI, cdc25c assoxiated protein kinase |
| 13 | U28386 | -4.8 | 0.58 | 77 | 928 | 541 | hSRPIα, NLS receptor |
| 14 | X02910 | -4.8 | 0.37 | 20 | 170 | 63 | tumor necrosis factor (TNF-α) |
| 15 | D31764 | -4.7 | 0.26 | 36 | 247 | 64 | hEphB1b, Eph-like receptor tyrosine kinase |
| 16 | X67155 | -4.4 | 0.30 | 28 | 199 | 60 | MKLP-1, mitotic kinesin-like protein-1 |
| 17 | HG3523 | -4.4 | 0.51 | 40 | 391 | 200 | c-Myc, alternate splice form 3 |
| 18 | Z15005 | -4.2 | 0.28* | 10 | 36 | -20 | CENP-E putative kinetochore motor |

*To compute $r(i) = x_I(i)/x_U(i)$, negative levels of expression were reset to a value of 10.
†Genes previously reported to respond transcriptionally to ionizing radiation.
Gene functions: Black = cell cycle; Dark gray = apoptosis; Light gray = DNA repair

What is claimed is:

1. A method for analyzing a plurality of sets of values associated with a plurality of genes to identify genes whose associated values differ by an amount of statistical significance among the sets, said associated values comprising levels of mRNA or protein, said associated values acquired by a process where biological samples containing said plurality of genes are hybridized to one or more microarrays of probes, thus measuring the levels of mRNA or protein in the biological samples, wherein the method comprises:

providing for each of the plurality of genes a parameter that contains information concerning differences in the associated values of that gene among the sets;

adjusting the parameters of the plurality of genes so that variables related to the parameters are substantially independent of variations of scatter values or average associated values of the genes over the sets, said scatter values defined by the standard deviation of the associated values in the sets;

deriving an observed value and an expected value of the adjusted parameter for each gene from the sets of associated values, said expected value being indicative of the extent of variations in the adjusted parameter introduced by the process;

comparing the observed and expected values of the parameter to identify genes whose associated values differ by an amount of statistical significance among the sets; and providing for use by a user a list of genes whose associated values differ by an amount of statistical significance among the sets.

2. The method of claim 1, wherein said adjusting includes:
dividing the scatter values or average associated values of the genes into subsets each having a similar range of values, and calculating the standard deviation of each of the parameters within each subset;
altering the parameters until a coefficient of variation of the standard deviations of the parameters among the subsets is minimized.

3. The method of claim 1, further comprising obtaining said sets of associated values from multiple measurements of the plurality of genes, or values derived therefrom.

4. The method of claim 1, wherein said sets of associated values represent gene expression or number of gene copies or levels of protein encoded by the genes.

5. The method of claim 1, wherein said sets of associated values include calculated or predicted values.

6. The method of claim 1, wherein said providing a parameter includes calculating a difference value between an associated value of each gene in a first of the sets or a value derived therefrom and an associated value of that gene in a second of the sets or a value derived therefrom; and
wherein the parameter is a function of the difference value of that gene.

7. The method of claim 6, wherein said providing a parameter further includes:
generating for each of the plurality of genes a scatter value that quantifies variation in the associated values of that gene within the first and second sets; and
wherein said parameter is a function of the scatter value and of the difference value, said parameter defining a relative difference value of that gene.

8. The method of claim 7, wherein said generating employs the following equation:

$$s(i) = \left( \{1/a\} \left\{ \sum_m [x_m(i) - \underline{x}_I(i)]^2 + \sum_n [x_n(i) - x_U(i)]^2 \right\} \right)^{1/2}$$

where gene (i) has associated values $x_I(i)$ and $x_U(i)$ in Ith and Uth states respectively in the first and second sets of associated values, I and U being positive integers; $\Sigma_m$ and $\Sigma_n$ are sums over associated values of gene (i) in states I in the first set and in states U in the second set respectively, where s(i) is the scatter value of gene (i), and a is a constant.

9. The method of claim 8, wherein said calculating calculates the parameter d(i) from the following equation:

$$d(i) = [\underline{x}_I(i) - \underline{x}_U(i)]/[s(i) + s_0]$$

where $s_0$ is a constant, and $\underline{x}_I(i)$ and $\underline{x}_u(i)$ are the average values of $x_I(i)$ and $x_U(i)$ respectively in the first and second sets of associated values.

10. The method of claim 9, said adjusting comprising:
dividing the scatter values or average associated values of the genes into subsets each having a similar range of values, and calculating the standard deviation of each of the parameters within each subset; and
altering value of $s_0$ until a coefficient of variation of the standard deviations of the parameters among the subsets is minimized.

11. The method of claim 1, wherein said associated values of the genes are correlated with another variable so that each of said associated values has a corresponding value of the variable, and wherein the parameter is provided using a Pearson correlation coefficient related to a weighted difference between each of the associated values and an average associated value, the variance of the associated values and the variance of the variable, said difference weighted by the deviation of the corresponding value of the variable of such associated value from its average value.

12. The method of claim 11, wherein said variable is continuous.

13. The method of claim 12, wherein said variable is time.

14. The method of claim 11, wherein the parameter is selected using the Pearson correlation coefficient and a quantity $s_0$ that has a value adjusted in said adjusting as follows:
dividing the scatter values or average associated values of the genes into subsets each having a similar range of values, and calculating the standard deviation of each of the parameters within each subset; and
altering the value of $s_0$ until a coefficient of variation of the standard deviations of the parameters among the subsets is minimized.

15. The method of claim 11, the number of sets of associated values being k, k being a positive integer, wherein said Pearson correlation coefficient r(i) is given by:

$$r(i) = \sum_k [(x_k(i) - \underline{x}(i))][(y_k - \underline{y})] \Big/ \sqrt{\sum_k (x_k(i) - \underline{x}(i))^2 \sum_k (y_k - \underline{y})^2}$$

where $X_k(1)$ is the associated value of gene (i) in the kth set of associated values, $\underline{x}(i)$ the average of the associated values of gene (i) in all the sets, $y_k$ the value of the variable corresponding to $x_k(i)$, $\underline{y}$ the average value of $y_k$ in all the sets, and $\Sigma_k$ is a sum over all values of k.

16. The method of claim 1, wherein the associated values in each set are classified into two or more subsets with values in each subset having a correlation with one another, and wherein the parameter is selected using a quantity related to the variances between the associated values in the subsets of the sets and the variances of the associated values within each subset of the sets.

17. The method of claim 16, wherein the quantity relates to the sum of the variances between the associated values in the subsets of the sets and the sum of the variances of the associated values within each subset of the sets.

18. The method of claim 17, wherein the parameter is selected using the Fisher discriminant and a quantity $s_0$ having a value which has been adjusted in said adjusting as follows:
dividing the scatter values or average associated values of the genes into subsets each having a similar range of values, and calculating the standard deviation of each of the parameters within each subset; and
altering value of $s_0$ until a coefficient of variation of the standard deviations of the parameters among the subsets is minimized.

19. The method of claim 18, wherein the number of subsets of associated values of such set being k, k being a positive integer, and the Fisher discriminant F(i) is given by:

$$F(i) = \sum_k n_k [\underline{x}_k(i) - \underline{x}(i)]^2 \Big/ \sum_k \sum_j [x_j(i) - \underline{x}_k(i)]^2$$

where $x_k(i)$ is an associated value of gene (i) in the kth subset of associated values, $\underline{x}_k(i)$ the average of the associated values of gene (i) in the kth subset, $\underline{x}(i)$ the average value of the associated values of gene (i) in all of the subsets, $n_k$ the number of associated values in the kth set, $\Sigma_j$ a sum over all the associated values of gene (i) in the kth subset, and $\Sigma_k$ a sum of the associated values of gene (i) over all of the subsets.

20. The method of claim 1, the sets of associated values referred to as original sets, wherein said deriving includes deriving said expected value by:

permuting, for each of the plurality of genes, the associated values for such gene in the original sets to arrive at a number of different permutations;

classifying the associated values in each permutation of each gene into corresponding permuted sets that are different from the original sets; and supplying for each permutation a parameter value of each of the genes derived from an associated value of such gene in each of the corresponding permuted sets for such permutation or values derived therefrom.

21. The method of claim 20, wherein said associated values of the genes are correlated with another variable so that each of said associated values has an associated value of the variable, wherein the permuting permutes the associated values so that at least each of some of the associated values has a different associated variable.

22. The method of claim 21, wherein the associated values are classified into two or more subsets with values in each subset having a correlation with one another, wherein the permuting permutes the associated values so that at least each of some of the associated values is in a subset different from the subset it is classified into.

23. A method for analyzing a plurality of original sets of values associated with a plurality of genes to identify genes whose associated values differ by an amount of statistical significance among the sets, said associated values comprising levels of mRNA or protein, said associated values acquired by a process where biological samples containing said plurality of genes are hybridized to one or more microarrays of probes, thus measuring the levels of mRNA or protein in the biological samples, wherein the method comprises:

calculating for each of the plurality of genes a value for a statistical parameter indicating differences between associated values of such gene among the original sets;

ranking the values of the parameter of the genes;

providing an expected value of such parameter for each rank, wherein said providing includes permuting the associated values in the original sets to arrive at sets different from the original sets for each permutation, deriving a value of such parameter for each permutation, and ranking such values, said expected value for each rank being indicative of the extent of variations in the parameter for parameters in said rank introduced by the process;

comparing the calculated and expected values for the parameter of the same rank to identify genes whose associated values differ by an amount of statistical significance among the sets; and providing for use by a user a list of genes to a user whose associated values differ by an amount of statistical significance among the sets.

24. The method of claim 23, wherein said providing comprises:

for each permutation, deriving a value of the parameter for each gene and ranking the genes by their associated parameter values; and determining the expected value of such parameter for each rank by computing an average value of the parameter of all the permutations having such rank.

25. The method of claim 24, wherein said comparing comprises identifying a gene as one whose associated values differ by an amount of statistical significance among the sets when the difference for such gene between the calculated value of the parameter of a rank and the expected value of such parameter of the same rank exceeds a threshold.

26. The method of claim 23, wherein the sets of associated values in each permutation contains approximately an equal number of associated values from each of the original sets of associated values.

27. A computer readable storage device embodying a program of instructions executable by a computer to perform a method for analyzing a plurality of sets of values associated with a plurality of genes to identify genes whose associated values differ by an amount of statistical significance among the sets, said associated values comprising levels of mRNA or protein, said associated values acquired by a process where biological samples containing said plurality of genes are hybridized to one or more microarrays of probes, thus measuring the levels of mRNA or protein in the biological samples, wherein the method comprises:

providing for each of the plurality of genes a parameter that contains information concerning differences in the associated values of that gene among the sets;

adjusting the parameters of the plurality of genes so that variables related to the parameters are substantially independent of variations in scatter values or average associated values of the genes over the sets, said scatter values defined by standard deviation of the associated values in the sets;

deriving an observed value and an expected value of the adjusted parameter for each gene from the sets of associated values, said expected value being indicative of the extent of variations in the adjusted parameter introduced by the process;

comparing the observed and expected values of the parameter to identify genes whose associated values differ by an amount of statistical significance among the sets; and providing for use by a user a list of genes whose associated values differ by an amount of statistical significance among the sets.

28. A computer readable storage device embodying a program of instructions executable by a computer to perform a method for analyzing a plurality of original sets of values associated with a plurality of genes to identify genes whose associated values differ by an amount of statistical significance among the sets, said associated values comprising levels of mRNA or protein, said associated values acquired by a process where biological samples containing said plurality of genes are hybridized to one or more microarrays of probes, thus measuring the levels of mRNA or protein in the biological samples, wherein the method comprises:

calculating for each gene a value for a statistical parameter indicating differences between associated values of such gene among the original sets;

ranking the values of the parameter of the genes;

providing an expected value of such parameter for each rank, wherein said providing includes permuting the associated values in the original sets to arrive at sets different from the original sets for each permutation, deriving a value of such parameter for each permutation, and ranking such values, said expected value for each rank being indicative of the extent of variations in the parameter for parameters in said rank introduced by the process;

comparing the calculated and expected values for the parameter of the same rank to identify genes whose associated values differ by an amount of statistical significance among the sets; and providing for use by a user a list of genes whose associated values differ by an amount of statistical significance among the sets.

29. A computer system for analyzing a plurality of sets of values associated with a plurality of genes to identify genes whose associated values differ by an amount of statistical significance among the sets, said associated values comprising levels of mRNA or protein, said associated values acquired by a process where biological samples containing said plurality of genes are hybridized to one or more microarrays of probes, thus measuring the levels of mRNA or protein in the biological samples, wherein the system comprises:

one or more computers;

one or more computer programs running on the computer(s), performing the following:

providing for each of the plurality of genes a parameter that contains information concerning differences in the associated values of that gene among the sets;

adjusting the parameters of the plurality of genes so that variables related to the parameters are substantially independent of variations in scatter values or average associated values of the genes over the sets, said scatter values defined by standard deviation of the associated values in the sets;

deriving an observed value and an expected value of the adjusted parameter for each gene from the sets of associated values, said expected value being indicative of the extent of variations in the adjusted parameter introduced by the process;

comparing the observed and expected values of the parameter to identify genes whose associated values differ by an amount of statistical significance among the sets; and providing for use by a user a list of genes whose associated values differ by an amount of statistical significance among the sets.

30. A computer system for analyzing a plurality of original sets of values associated with a plurality of genes to identify genes whose associated values differ by an amount of statistical significance among the sets, said associated values comprising levels of mRNA or protein, said associated values acquired by a process where biological samples containing said plurality of genes are hybridized to one or more microarrays of probes, thus measuring the levels of mRNA or protein in the biological samples, wherein the system comprises:

one or more computers;

one or more computer programs running on the computer(s), performing the following:

calculating for each gene a value for a statistical parameter indicating differences between associated values of such gene among the original sets;

ranking the values of the parameter of the genes;

providing an expected value of such parameter for each rank, wherein said providing includes permuting the associated values in the original sets to arrive at sets different from the original sets for each permutation, deriving a value of such parameter for each permutation, and ranking such values, said expected value for each rank being indicative of the extent of variations in the parameter for parameters in said rank introduced by the process;

comparing the calculated and expected values for the parameter of the same rank to identify genes whose associated values differ by an amount of statistical significance among the sets; and providing for use by a user a list of genes whose associated values differ by an amount of statistical significance among the sets.

* * * * *

UNITED STATES PATENT AND TRADEMARK OFFICE
CERTIFICATE OF CORRECTION

| | | |
|---|---|---|
| PATENT NO. | : 7,363,165 B2 | Page 1 of 1 |
| APPLICATION NO. | : 09/811762 | |
| DATED | : April 22, 2008 | |
| INVENTOR(S) | : Tusher et al. | |

It is certified that error appears in the above-identified patent and that said Letters Patent is hereby corrected as shown below:

Under Column 1:

• Please insert at line 11:

-- FEDERALLY-SPONSORED RESEARCH OR GOVERNMENT
This invention was made with Government support under contracts CA77302 and CA075675 awarded by the National Institutes of Health. The Government has certain rights in this invention. --

Signed and Sealed this
Thirteenth Day of March, 2012

David J. Kappos
*Director of the United States Patent and Trademark Office*